United States Patent [19]

Mizuguchi et al.

[11] Patent Number: 4,861,839
[45] Date of Patent: Aug. 29, 1989

[54] METAL CHELATE COMPOUND AND CURABLE COATING COMPOSITION THEREFROM

[75] Inventors: Katsumi Mizuguchi, Suita; Yoshitaka Okude, Hirakata; Hiroshi Miwa, Itami; Hidefumi Okuda, Toyonaka, all of Japan

[73] Assignee: Nippon Paint Co., Ltd., Osaka, Japan

[21] Appl. No.: 207,143

[22] Filed: Jun. 15, 1988

[30] Foreign Application Priority Data

Jun. 15, 1987 [JP] Japan .................. 62-148766

[51] Int. Cl.$^4$ ............................. C08G 59/70
[52] U.S. Cl. ........................ 525/506; 528/90; 528/92; 528/411; 528/413; 528/416; 556/9; 556/12
[58] Field of Search ............ 528/90, 92, 411, 413, 528/416; 556/9, 12; 525/506

[56] References Cited

U.S. PATENT DOCUMENTS

| | | |
|---|---|---|
| 3,812,214 | 5/1974 | Markovitz .................. 528/92 |
| 4,113,791 | 9/1978 | Smith et al. ............. 528/92 X |
| 4,116,886 | 9/1978 | Cella ..................... 528/92 X |
| 4,196,138 | 4/1980 | Cella ..................... 556/9 X |
| 4,322,513 | 3/1982 | Wada et al. .............. 528/92 X |
| 4,406,764 | 9/1983 | Hayase et al. ............ 528/92 X |

FOREIGN PATENT DOCUMENTS 1202787  10/1965  Fed. Rep. of Germany.

Primary Examiner—Earl Nielsen
Attorney, Agent, or Firm—Wenderoth, Lind & Ponack

[57] ABSTRACT

A metal chelate compound in which a chelate forming metal is coordinated with a ligand represented by the formula

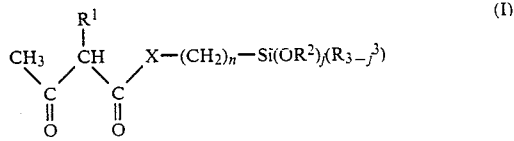

wherein $R^1$, $R^2$ and $R^3$, which are the same or different, represent a hydrogen atom or an alkyl group having 1 to 3 carbon atoms, X represents —$NR^4$— (wherein $R^4$ represents a hydrogen atom or an alkyl group having 1 to 3 carbon atoms), an oxygen atom or a sulfur atom, n is an integer of 1 to 3, and j is an integer of 1 to 3, and a coating composition containing the same.

5 Claims, No Drawings

METAL CHELATE COMPOUND AND CURABLE COATING COMPOSITION THEREFROM

FIELD OF THE INVENTION

The present invention relates to a novel chelate compound and a curable coating composition containing the same.

BACKGROUND OF THE INVENTION

Hitherto, there has been known a silane coupling agent which enhances adhesion between an inorganic material and an organic material. Since the silane coupling agent has a group reactive with an inorganic material and another group reactive with an organic material in one molecule, chemical bonds are formed through the groups to result in enhancing adhesion.

A metal chelate compound is also used for improving compatibility between a resin binder and an inorganic pigment in coating compositions. This compound chemically binds to both an organic material and an inorganic material so as to perform the improvement.

However, in actual usages, neither silane coupling compound nor metal chelate compound is still sufficient in adhesion and compatibility.

On the other hand, there are known tri(trialkylsiloxy)aluminum or a metal chelate/silicon compound as a catalyst for epoxy cationic polymerization. It is generally formulated into a sealing compound for electronic elements. However, it can not be used in a coating composition because it adversely affects storage stability and coating appearance.

SUMMARY OF THE INVENTION

The present invention is to provide a novel metal chelate compound in which a chelate forming metal is coordinated with a ligand represented by the formula

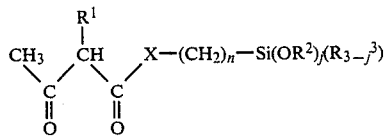 (I)

wherein $R^1$, $R^2$ and $R^3$, which are the same or different, represent a hydrogen atom or an alkyl group having 1 to 3 carbon atoms, X represents $-NR^4-$ (wherein $R^4$ represents a hydrogen atom or an alkyl group having 1 to 3 carbon atoms), an oxygen atom or a sulfur atom, n is an integer of 1 to 3, and j is an integer of 1 to 3. The metal chelate compound of the present invention has two sorts of reactive groups, one of which forms a chemical bond with an organic material and the other does so with an inorganic material and, if one of them is bonded to the inorganic material, the other remains in a condition free from steric hindrance to easily react with the organic material, such as a resin binder.

The present invention also is to provide a curable coating composition comprising the chelate compound of the present invention and an epoxy resin.

DETAILED DESCRIPTION OF THE INVENTION

The ligand having the formula (I) employed in the present invention can be prepared by reacting a diketene or acetoacetic acid with a silicon compound having both an amino group (including an imino group), an alcohol group or a thiol group, and a hydrolyzable group. Examples of the silicon compounds arethose having an amino or imino group, such as gamma-aminopropyltrimethoxysilane, gamma-aminopropyltriethoxysilane, gamma-aminopropyltripropoxysilane, N-phenyl-gamma-aminopropyltrimethoxysilane, N-phenyl-gamma-aminopropyltriethoxysilane and N-phenyl-gamma-aminopropyltripropoxysilane and the like; those having an alcohol group, such as silyl alcohol, 3-butene-1-ol, 3-butene-2-ol, 4-pentene-1-ol, 4-pentene-2-ol; those having a thiol group, such as gamma-mercaptoproyltrimethoxysilane, gamma-mercaptopropyltriethoxysilane, gamma-mercaptopropylpropoxysilane and the like. The reaction may generally be carried out at 0° to 100° C., preferably 40° to 80° C., in an organic solvent. Examples of the organic solvents are halogenated alkyls, such as chloroform, methylene chloride, dichloroethane and the like; cyclic ethers, such as tetrahydrofuran, dioxane and the like; esters, such as ethyl acetate, butyl acetate and the like; aromatic compounds, such as benzene, xylene and the like.

The ligand of the present invention can also be prepared by reacting an alpha, gamma-diketo compound having a carbon-carbon double bond with a silylhydrite compound by a method as disclosed by J. Amer. Chem. Soc. 82, 3601 (1960).

The chelate forming metal of the present invention includes aluminum, magnesium, zirconium, titanium, iron, cobalt, nickel, chromium or manganese. Preferred is aluminum, zirconium or titanium.

A method of forming a chelate compound is known, including a method using a metal alkoxide, a ligand-exchanging method using another metal chelate, a method using a metal chloride (Rocz. Chem., 44, 1363 (1970)), a method using a metal oxide (Indian J. Chem., 4, 451, (1966)) and a method directly synthesizing from a metal (Nippon Kagaku Zasshi, 84, 890 (1966)) and the like. Formation of the chelate compound of the present invention can be identified by existence of absorption which is formed by chelate formation.

The obtained chelate compound of the present invention is very suitable for a coating composition containing an epoxy resin, because it can be formulated to high a solid type composition and the obtained coating has a good appearance. The epoxy resin is one having at least one oxirane group in one molecule on an average, such as bisphenol A type epoxy resin, bisphenol F type epoxy resin, hydrogenated bisphenol A type epoxy resin, phenol-novolak type epoxy resin, cresol-novolak type epoxy resin, aliphatic glycidyl ether type epoxy resin, alicyclic epoxy resin, heterocyclic epoxy resin and the like. Also, a monoepoxy compound, such as phenyl, glycidyl ether, butyl glycidyl ether, phenoxy ether type monoepoxide or cyclohexaneoxide may be employed in combination with the above mentioned epoxy resin.

The amount of the chelate compound in the coating composition may be, for example, 0.1 to 20% by weight based on the amount of the epoxy resin.

The coating composition may contain a liquid diluent. By "liquid diluent" is meant a solvent or non-solvent which is volatile and evaporated after coating and which reduces to a viscosity sufficientto coat it in a uniform and controlled thickness by a simple coating method, such as spraying. Also, the liquid diluent assists wetting characteristics, compatibility with a polymer component, package stability, coalescence or film formation. Suitable diluents include aromatic hydrocarbons, such as toluene and xylene; ketones, such as methyl ethyl ketone and methyl isobutyl ketone; alcohols, such as isopropyl alcohol and n-butyl alcohol; monoethers of a glycol, such as monoethers of ethylene glycol or diethylene glycol; monoether glycol acetates, such as 2-ethoxyethyl acetate; a mixture thereof. The diluent can be present in an amount of up to 60% by weight, preferably 20 to 40% by weight based on the total amount of the diluent and nonvolatile content of the coating composition.

The above components may be formulated to form a clear coating composition or combined with a pigment to form a paint. The pigment can be any conventional one, for example iron oxide, lead oxide, strontium chromate, carbon black, coal dust, titanium dioxide, talc, barium sulfate or a color pigment, such as cadmium yellow, cadmium red, chromium yellow, and a metal pigment, such as aluminum flake and the like.

The pigment content of the paint is usually expressed as pigment-to-nonvolatile weight ratio. In the practice of the present invention, pigment-to-nonvolatile weight ratios are as high as 2:1, but typically within the range of 0.05 to 1:1.

In addition to the above component, a filler, a plasticizer, an antioxidant, a ultraviolet absorber, a flow controlling agent, a surfactant and another additive may be formulated into the coating composition, if desired. The additives may be varied greatly and can be up to about 10% by weight based on the nonvolatile content of the coating composition.

The coating composition can be applied by spraying, brushing, dipping, rolling, flowing and the like. The coating composition is applicable to any substrate, such as wood, metal, glass, fabric, plastics, foamed material and the like, or any primered coated surface. Preferred is plastics or metal (such as steel or aluminum).

A dry film thickness can be varied depending upon its usages, but is usually 0.5 to 3 mil, preferably 1 to 2 mil.

After being coated on a substrate, the coated composition is cured. Curing can be carried out at any temperature including ambient temperature, but the coating composition of the present invention can be cured at a low temperature, especially 50° to 150° C., preferably 60° to 100° C. to obtain a highly crosslinked cured film. Curing time is also varied depending on curing temperature and the like, but is suitably 10 to 30 minutes at 60° to 100° C.

The chelate compound of the present invention has more than two reactive groups which form chemical bonds with an organic and inorganic materials and which are free from steric hindrance. The coating composition containing the chelate compound of the present invention is excellent in storage stability and a coating therefrom has excellent appearance and hardness and also excellent smoothness. The coating composition is suitable for coating of automobiles, plastics, electronic elements and the like and is worthwhile in modern industry.

EXAMPLES

The present invention is illustrated by the following examples, which are not to be construed as limiting the scope of the invention to their details.

EXAMPLE 1

Synthesis of a ligand (I)

A one liter reaction vessel equipped with a thermometer, a condenser and a dropping funnel was charged with 58 g (1 mol) of allyl alcohol, 100 g of dioxane and 0.41 g of sodium acetate (catalyst) under nitrogen blanket and heated to 60° C., to which 84 g (1 mol) of diketene was added dropwise for one hour. After completion of the addition, it was allowed to react for 2 hours with heating and dioxane was removed at a reduced pressure. The reaction product was further distilled to obtain 2-propenyl acetoacetate. It was identified by absorption at 1,742, 1,721 and 1,684 $cm^{-1}$ in IR spectrum.

Next, the obtained 2-propenyl acetoacetate was addition-reacted with trimethoxysilane according to a method described in J. Amer. Chem. Soc., 82, 3601 (1960) to obtain gamma-trimethoxysilylpropyl acetoacetate having the following characteristics:

IR Spectrum: Absorptionat 1,190, 1,080 and 820 $cm^{-1}$ which is derived from trimethoxysilane.

NMR Spectrum Solvent; $CDCl_3$ Internal standard; TMS.

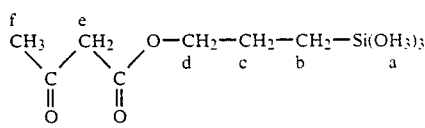

Preparation of a metal chelate compound

A one liter reaction vessel equipped with a thermometer, a condenser and a dropping funnel was charged with 68 g (⅓ mol) of aluminum isopropoxide and 350 g of benzene under nitrogen blanket, to which 264 g (1 mol) of gamma-trimethoxysilylpropyl acetoacetate was added dropwise from the dropping funnel for 30 minutes. After completion of the addition, it was allowed to react for 30 minutes at 60° C. and benzene and isopropyl alcohol which as produced in the reaction were distilled away to obtain 237 g of a chelate compound having a high viscosity. It was identified by absorption at 1,606 and 1,525 $cm^{-1}$ in IR spectrum which is derived from chelate formation.

EXAMPLE 2

Synthesis of a ligand (I)

The same reaction vessel as Example 1 was charged with 179 g (1 mol) of gamma-aminopropyltrimethoxysilane and 200 ml of methylene chloride under nitrogen blanket and cooled in an ice bath, to which 84 (1 mol) of diketene was added dropwise. After completion of the addition, it was returned to room temperature and allowed to react for 30 minutes. Then, methylene chloride and unreacted material were remioved at a reduced pressure. The reaction product has the following characteristics:

IR Spectrum: Absorption at 1,722, 1,650, 1,550, 1,190, 1,080 and 820 $cm^{-1}$ which is derived from acetoacetamide and trimethoxysilane.

NMR Spectrum Solvent; $CDCl_3$ Internal standard; TMS.

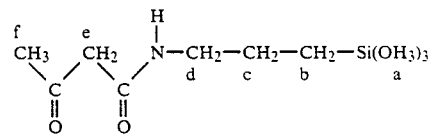

Preparation of a metal chelate compound

The same reaction vessel as in Example 1 was charged with 68 g (⅓ mol) of aluminum isopropoxide and 350 g of benzene under nitrogen blanket, to which 88 g (⅓ mol) of gamma-trimethoxysilylpropyl acetoacetamide was added dropwise and then 67 g (⅔ mol) of acetyl acetone was added dropwise. After completion of the addition, it was allowed to react for 30 minutes at 60° C. and benzene and isopropyl alcohol which was produced in the reaction were distilled away to obtain 164 g of a chelate compound having a high viscosity. It was identified by absorption at 1,610 and 1,570, 1,480 and 1,420 cm$^{-1}$ in IR spectrum which is derived from chelate formation.

EXAMPLE 3

Synthesis of a ligand (I)

A same reaction vessel as Example 1 was charged with 196 g (1 mol) of gamma-mercaptopropyltrimethoxysilane,. 200 ml of benzene and one gram of triethylamine under nitrogen blanket and heaed to 60° C., to which 84 g (1 mol) of diketene was added dropwise for one hour. After completion of the addition, it was allowed to react for 30 minutes. Then, benzene chloride and the unreacted materials were removed at a reduced pressure. The reaction product has the following characteristics:

IR Spectrum: Absorption at 1,720, 1,680, 1,560, 1,190, 1,080 and 820 cm$^{-1}$ which is derived from acetylthioacetate and trimethoxysilane.

NMR Spectrum Solvent; CDCl$_3$ Internal standard; TMS.

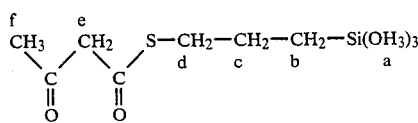

Preparation of a metal chelate compound

A same reaction vessel as Example 1 was charged with 68 g (⅓ mol) of aluminum isopropoxide and 350 g of benzene under nitrogen blanket, to which 178 g (⅔ mol) of gamma-trimethoxysilylpropyl acetothioacetate was added dropwise and then 43 g (⅓ mol) of ethyl acetoacetate was added dropwise. After completion of the addition, it was allowed to react for 30 minutes at 60° C. and benzene and isopropyl alcohol which was produced in the reaction were distilled away to obtain 239 g of a chelate compound having a high viscosity. It was identified by absorption at 1,610 and 1,570 and 1,505 cm$^{-1}$ in IR spectrum which is derived from chelate formation.

EXAMPLE 4

One hundred parts by weight of an alicyclic epoxy resin (3,4-epoxycyclohexylmethyl-3,4-epoxycyclohexane carboxylate) and 3 parts by weight of the methoxysilane containing aluminum chelate prepared in Example 1 were mixed to form a clear coating composition.

EXAMPLES 5 TO 6

Ingredients shown in Table 1 were formulated in the amount ratio shown in Table 1 to form clear coating compositions.

COMPARATIVE EXAMPLE 1

A clear coating composition was prepared as generally described in Example 4 with the exception that 1.5 parts by weight of aluminum tris(acetylacetate) and KR-213 (silicone varnish available from Shinetsu Chemical Industries Inc.) were employed instead of the metal chelate compound of the present invention.

Each coating composition in Examples 4 to 6 and Comparative Example 1 was diluted with a 50/50 mixture of butyl acetate and xylene to a spray viscosity and applied to a phosphate pretreated steel panel. It was baked at 100° to 150° C. for 30 minutes. The film properties are shown in Table 1. A storage stability test was carried out by storing the clear coating composition adjusted to an initial viscosity of 60 Ku at 40° C. for 3 months and the result is shown in Table 1.

TABLE 1

| Ingredients | Examples 4 | Examples 5 | Examples 6 | Comparative Ex 1 |
|---|---|---|---|---|
| 3,4-Epoxycyclohexylmethyl-3,4-epoxycyclohexane carboxylate | 100 | 80 | 50 | — |
| 4,5-Di(octylcarboxyl) cyclohexeneoxide | — | 20 | — | — |
| Epicoto 154* | — | — | 50 | — |
| Metal chelate compound | Example 1 | Example 2 | Example 3 | — |
| (parts by weight) | (3) | (10) | (17) | — |
| Coating appearance | Good | Good | Good | Shrinkage |
| Storage stability | 63 | 66 | 62 | Gelation |
| Curing temperature (°C.) | 100 | 100 | 150 | 100 |

What is claimed is:

1. A metal chelate compound in which a chelate forming metal is coordinated with a ligand represented by the formula

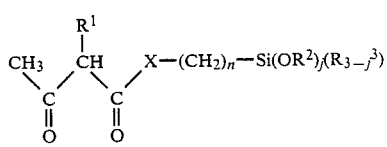

wherein R$^1$, R$^2$ and R$^3$, which are the same or different, represent a hydrogen atom or an alkyl group having 1 to 3 carbon atoms, X represents —NR$^4$— (wherein R$^4$ represents a hydrogen atom or an alkyl group having 1 to 3 carbon atoms), an oxygen atom or a sulfur atom, n is an integer of 1 to 3, and j is an integer of 1 to 3.

2. The metal chelate compound according to claim 1 wherein said chelate forming metal is aluminum, magnesium, zirconium or titanium.

3. The metal chelate compound according to claim 1 wherein R$^1$ of said formula is a hydrogen atom.

4. A curable coating composition comprising;
   (A) a metal chelate compound in which a chelate forming metal is coordinated with a ligand represented by the formula

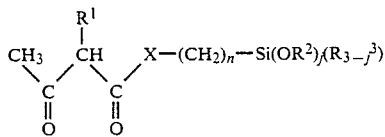

wherein $R^1$, $R^2$ and $R^3$, which are the same or different, represent a hydrogen atom or an alkyl group having 1 to 3 carbon atoms, X represents —$NR^4$— (wherein $R^4$ represents a hydrogen atom or an alkyl group having 1 to 3 carbon atoms), an oxygen atom or a sulfur atom, n is an integer of 1 to 3, and j is an integer of 1 to 3, and (B) an epoxy resin.

5. The curable coating composition according to claim 4 wherein said chelate compound is present in the coating composition in an amount of 0.1 to 20% by weight based on the amount of the epoxy resin.

* * * * *